United States Patent [19]

Liang

[11] 4,201,719

[45] May 6, 1980

[54] PRECIOUS METAL NITROGENOUS ORGANO REACTION PRODUCTS

[75] Inventor: Anthony Liang, Half Moon Bay, Calif.

[73] Assignee: GTE Sylvania Incorporated, Stamford, Conn.

[21] Appl. No.: 844,380

[22] Filed: Oct. 21, 1977

[51] Int. Cl.$^2$ ............................ C07F 1/12; C07F 15/00
[52] U.S. Cl. ................... 260/429 R; 260/414; 260/430; 548/101
[58] Field of Search ............ 260/430, 414, 429 R, 260/299

[56] References Cited

U.S. PATENT DOCUMENTS

| | | | |
|---|---|---|---|
| 2,065,418 | 12/1936 | Andersag et al. | 260/430 X |
| 2,132,505 | 10/1938 | Williams et al. | 260/429 R X |
| 2,150,349 | 3/1939 | Van Peski et al. | 260/438.1 |
| 2,584,861 | 2/1952 | Garner et al. | 260/438.1 |
| 3,038,904 | 6/1962 | Godfrey | 260/268 |
| 3,255,222 | 6/1966 | Horowitz | 260/430 X |
| 3,372,135 | 3/1968 | Wada et al. | 260/439 R X |
| 3,458,544 | 7/1969 | Bryan | 260/430 X |
| 3,558,520 | 1/1971 | Kubicek et al. | 260/429 R X |
| 3,652,613 | 3/1972 | Wright | 260/429 R |
| 3,803,158 | 4/1974 | Chambers | 260/299 |

OTHER PUBLICATIONS

Leh et al., J. of Pharmaceutical Sciences, vol. 65, No. 3 (1976), p. 319.

*Primary Examiner*—Helen M. S. Sneed
*Attorney, Agent, or Firm*—Donald R. Castle

[57] ABSTRACT

A composition consisting essentially of reaction products of an ammonium salt of an aliphatic acid and a gold complex of a reactive nitrogen-containing organic compounds is soluble in organic solvents and can be used for various purposes including decorating substrates and in the manufacture of printed circuit boards. Typical reaction products include the reaction product of ammonium decanoate and the gold or platinum complex of 1, 2-diaminopropane. The process for producing the composition involves reacting a precious metal salt with a reactive nitrogen containing organic compound to form the precious metal complex and reacting an organic nitrogen compound containing a reactive nitrogen group such as an amino group and an aliphatic acid to form an ammonium salt of an aliphatic acid. Thereafter the ammonium salt is reacted with the precious metal nitrogen organo complex to form the compositions of this invention.

19 Claims, No Drawings

PRECIOUS METAL NITROGENOUS ORGANO REACTION PRODUCTS

BACKGROUND OF THE INVENTION

1. Field of the Invention

This invention relates to precious metal containing materials that can be used in electroplating. More particularly it relates to the reaction product of an ammonium salt of an aliphatic acid and a gold complex of a reactive nitrogen-containing organic compound.

2. Prior Art

With the exception of the triazolyl gold compounds disclosed in U.S. Pat. No. 3,803,158, most precious metal compounds used for the production of decorative gold films on substrates generally contain sulfur. When the complexes containing the sulfur are decomposed by heat, the precious metal such as gold is deposited upon the substrate but objectionable vapors containing sulfur compounds such as $H_2S$ and $SO_2$ are evolved. Additionally, when the raw materials for the product of precious metal decomposable compounds are prepared, if a sulfur bearing compound is used, waste disposal of the by-products becomes a problem even if the precious metal compound does not contain sulfur. Thue even though the triazoyl gold compounds of U.S. Pat. No. 3,803,158 do not yield sulfur bearing gases, the dimethyl sulfide by-product presents a disposal problem.

It is believed, therefore, that a precious metal containing organic product that can be decomposed by heat to the metal and a volatile non-sulfur containing compound that is prepared from sulfur free raw materials would be an advancement in the art.

OBJECTS AND SUMMARY OF THE INVENTION

It is an object of this invention to provide a non-sulfur-containing precious-metal-containing organic compound useful for decorating substrates.

It is an additional object of this invention to provide a heat decomposable precious metal-containing compound that is prepared from sulfur-free raw materials.

It is a further object of this invention to provide a precious metal nitrogenous organo reaction product that can be decomposed by heat to form the metal and volatile by-products.

It is still another object of this invention to provide an economical process for producing a sulfur-free precious metal nitrogenous reaction product of an ammonium salt of an aliphatic acid and a gold complex of a reactive nitrogen containing organic compound.

These and other objects are achieved in one aspect of this invention by providing a composition consisting essentially of the water insoluble reaction product of an ammonium salt of an aliphatic acid and a gold complex of a reactive nitrogenous organic compound. In another aspect of this invention a process for producing the composition is provided that comprises reacting a precious metal salt with a reactive nitrogen containing organic compound to form a precious metal-nitrogen-organic complex, forming an ammonium salt of an aliphatic acid by reacting an organic nitrogen compound containing a reactive nitrogen with an aliphatic acid in water, separating the foregoing reaction products from their respective reaction media and reacting the precious metal complex and the ammonium salt of the aliphatic acid and separating the water-insoluble reaction product.

DETAILS OF THE PREFERRED EMBODIMENTS

For a better understanding of the present invention, together with other and further objects, advantages and capabilities thereof, reference is made to the following disclosure and appended claims in connection with the above description of some of the aspects of the invention.

If desired, the precious metal salts used as raw material, can be prepared by dissolving the precious metal in aqua regia and boiling with excess hydrochloric acid, thereby removing nitrogen oxides. The precious metal chloride is formed as a dark red syrup-like material that can be diluted with water and concentrated to a solution that contains from about 25% to 30% of the precious metal. Any water-soluble precious metal salt can be used however.

The reactive nitrogen-containing organic compounds that can be used in the practice of this invention include the primary, secondary and tertiary alkyl amines, the imidazoles and the amides. Any sulfur-free nitrogen organic compound that will react with a water soluble platinum or gold salt of inorganic acid to form a water insoluble platinum or gold complex can be used to practice this invention. One preferred class of nitrogenous organic compounds are the primary alkyl amines containing from about 2 to about 5 carbon atoms.

The aliphatic acids used in the practice of this invention are the mono carboxylic acids containing an alkyl chain having from about 4 to about 18 carbon atoms. Straight or branched chain aliphatic acids can be used. It is preferred that the alkyl chain contain from about 6 to about 12 carbon atoms.

To more fully describe the subject invention the following detailed examples are presented. All parts percentages and proportions are by weight unless otherwise indicated.

EXAMPLE 1

A gold chloride solution containing about 57 parts of gold is mixed with about 1000 parts of methanol. The solution is cooled in an ice-bath, and 70 parts of 1,2-diaminopropane are slowly stirred in within about 10 minutes. The slurry of gold-amine complex is stirred for about 30 minutes, and suction-filtered. The white solids are washed with methanol and sucked dry and are then dissolved in 500 parts of water.

An amine-carboxylate solution is made by dispersing about 200 parts of decanoic acid in about 800 parts water, and adding about 80 parts of 1,2-diaminopropane. The gold solution formed above is added to the amine-carboxylate solution and stirred for about ½ hour, and then allowed to stand for about 2 hours. A light orange oil separates from the aqueous phase. The oil is washed under agitation with three portions of about 400 parts of water, and dried in a vacuum oven at about 50° C. The gold resinate comes out as a reddish-orange viscous oil, with a typical gold content of about 15–17% by weight. The overall yield is about 60%. The gold resinate is soluble in xylene.

EXAMPLE 2

Gold solution is made by dissolving the metal in aqua regia and boiling down with hydrochloric acid to remove nitrogen oxides. Excess hydrochloric acid is removed by concentrating the solution to a dark red syrup, diluting with water, and concentrating again. Typically the solution contains about 25-20% gold.

About eighty parts of 2-ethyl-4-methylimidazole is dispersed in about 600 parts of water. Gold chloride solution containing about 28.5 parts of gold is diluted with about 200 parts of water, and stirred into the azole solution within about 5 minutes. A buff colored precipitate results. The solution is stirred for about another 10 minutes and then allowed to stand for about 10 to about 15 hours and the buff precipitate is filtered off by suction and washed with water. It is then re-slurried in about 400 parts of water under vigorous agitation.

About seventy parts of the azole is dispersed in about 400 parts of water, and about 90 parts of 2-ethylhexanoic acid stirred in. This results in a light brown emulsion. The emulsion is then stirred into the gold complex slurry. Stirring is maintained for about ½ hour, and the resinate formed allowed to settle out overnight. The viscous resinate is washed with three portions of warm (~40° C.) water of about 400 parts each by vigorous agitation, and dried in a vacuum oven at about 50°-60° C. After drying, the resinate is a deep red-brown oil and shows no haziness when viewed through light and is mixed with about a fourth of its volume of xylene to make it more liquid, and suction-filtered through coarse paper (Whatman's No. 54). Typical concentration is about 16-18%. Overall yield is about 65%.

The resinate is miscible with butyl carbitol acetate as well as xylene.

A typical analysis of the product is as follows:

| Au Resinate | % by weight |
|---|---|
| Au | 18.2 |
| C | 57.4 |
| H | 9.4 |
| N | 8.1 |
| Cl | 0.4 |
| O | 6.5 |

EXAMPLE 3

Platinum metal is dissolved in aqua regia by boiling, and the solution is boiled with hydrochloric acid to drive off nitrogen oxides until the platinum content is 35-40% by weight.

About 57 parts of platinum in the aforementioned solution is mixed with about 1000 parts of methanol. The solution is cooled in an ice bath, and about 120 parts of 1,2-diaminopropane stirred in within about 15 minutes. The solution is then warmed to about 50°-60° C. for about two hours while stirring is maintained, and the precipitated platinum complex is separated by filtering. The pale yellow platinum complex is rinsed with about 40 parts of methanol, and sucked dry by suction. The solid is then dissolved in about 800 parts of water, and the solution filtered to remove undissolved material.

The ammonium salt is made by dispersing about 280 parts of 2-ethylhexanoic acid into about 500 parts of water, and adding 125 parts of ammonium hydroxide. To this is added the aforementioned platinum complex solution within about 10 minutes. The mixture is stirred for about ½ hour, and the resinate is allowed to settle out for at least about two hours. The supernatant liquid is decanted off, and the resinate washed twice with about 400 parts of water, using vigorous agitation. Remaining water is removed in a vacuum oven heated to about 60° C. The resinate comes out as a honey-colored, viscous oil. Typical concentration is about 18% platinum. It is soluble in xylene, but insoluble in 2-ethylhexanoic acid.

A typical analysis of the product is as follows:

| Pt resinate | % by weight |
|---|---|
| Pt | 17.19 |
| C | 47.91 |
| H | 9.75 |
| N | 7.56 |
| Cl | 0.12 |
| O | 17.47 |

While there has been shown and described what are at present considered the preferred embodiments of the invention, it will be obvious to those skilled in the art that various changes and modifications may be made therein without departing from the scope of the invention as defined by the appended claims.

What is claimed is:

1. A composition consisting essentially of the reaction product of an ammonium salt of a monocarboxylic acid having an alkyl chain containing from about 6 to about 12 carbon atoms and a precious metal complex of a nitrogenous organic compound selected from primary, secondary and tertiary alkyl amines, imidazoles and amides wherein said precious metal is selected from gold and platinum.

2. The composition of claim 1 wherein said aliphatic acid is decanoic acid and said nitrogenous organic compound is 1,2-diaminopropane.

3. The composition of claim 1 wherein said aliphatic acid is 2-ethylhexanoic acid and said nitrogenous organic compound is 2-ethyl-4-methylimidazole.

4. A composition of claim 1 wherein said nitrogenous organic compound is an alkyl amine containing from about 2 to about 5 carbon atoms.

5. A composition according to claim 4 wherein said alkyl amine is 1,2-diaminopropane.

6. A composition according to claim 5 wherein said aliphatic acid is 2-ethylhexanoic acid.

7. A composition according to claim 4 wherein said precious metal is gold, said aliphatic acid is decanoic acid and said amine is 1,2-diaminopropane.

8. A composition according to claim 3 wherein said precious metal is gold.

9. A composition according to claim 5 wherein said precious metal is platinum and said acid is 2-ethylhexanoic acid.

10. A process comprising
   (a) reacting a precious metal salt, gold or platinum salt with a nitrogenous organic compound selected from primary, secondary and tertiary alkyl amines, imidazole and amides to form a precious metal-nitrogen-organic complex,
   (b) independently, reacting a nitrogenous organic compound with an aliphatic acid containing from 4 to 18 carbon atoms to form an ammonium salt of an aliphatic acid,
   (c) reacting said precious metal-nitrogen organic complex with said ammonium salt, and
   (d) separating the resulting water-insoluble-precious metal reaction product.

11. A process of claim 10 wherein said aliphatic acid is a monocarboxylic acid having an alkyl chain containing from about 6 to about 12 carbon atoms.

12. The process of claim 11 wherein said aliphatic acid is decanoic acid and said nitrogenous organic aliphatic compound is 1,2-diaminopropane.

13. The process of claim 11 wherein said aliphatic acid is 2-ethylhexanoic acid and said nitrogenous organic compound is 2-ethyl-4-methylimidazole.

14. A process of claim 10 wherein said nitrogenous organic compound is an alkyl amine containing from about 2 to about 5 carbon atoms.

15. A process according to claim 14 wherein said alkyl amine is 1,2-diaminopropane.

16. A process according to claim 15 wherein said aliphatic acid is 2-ethylhexanoic acid.

17. A process according to claim 14 wherein said precious metal is gold, said aliphatic acid is decanoic acid and said amine is 1,2-diaminopropane.

18. A process according to claim 13 wherein said precious metal is gold.

19. A process according to claim 15 wherein said precious metal is platinim and said acid is 2-ethylhexanoic acid.

* * * * *